United States Patent [19]
Madow et al.

[11] Patent Number: 6,080,121
[45] Date of Patent: *Jun. 27, 2000

[54] LAMINATED ORTHOPEDIC BRACE

[75] Inventors: Stephen R. Madow; Jim Kausek, both of Swampscott, Mass.

[73] Assignee: Becton, Dickinson and Company, Franklin Lakes, N.J.

[ * ] Notice: This patent is subject to a terminal disclaimer.

[21] Appl. No.: 09/335,353

[22] Filed: Jun. 17, 1999

[51] Int. Cl.⁷ ........................................................ A61F 5/00
[52] U.S. Cl. .................................. 602/5; 128/876; 602/19
[58] Field of Search ............................... 602/5, 6, 20, 21, 602/23, 26, 27, 60–65; 128/882, 876

[56] References Cited

U.S. PATENT DOCUMENTS

| | | | |
|---|---|---|---|
| 3,990,440 | 11/1976 | Gaylord | 602/63 |
| 4,084,586 | 4/1978 | Hettick | 602/63 |
| 4,090,508 | 5/1978 | Gaylord | 602/26 |
| 4,481,941 | 11/1984 | Rolfes | 602/19 |

*Primary Examiner*—Michael A. Brown
*Attorney, Agent, or Firm*—Alan W. Fiedler

[57] ABSTRACT

A laminated orthopedic brace made of a unique blend of material combining Airpreene™ material with Coolmax™ material as a liner. Airpreene™ material affords the properties of heat retention, compression and breathability, while Coolmax™ material wicks perspiration away from the skin and dries the area quickly. The combination of these materials provides compression and heat retention to the patient while providing wearing comfort.

3 Claims, 19 Drawing Sheets

LAMINATED ORTHOPEDIC BRACE

BACKGROUND OF THE INVENTION

1. Field of the Invention

The present invention relates to a laminated orthopedic brace and, more particularly, to a laminated orthopedic made from a unique blend of material that provides heat retention, compression with breathability, and wicking of perspiration away from the skin to dry the skin area quickly.

2. Background Description

A wide variety of externally applied elastic supports and rigid, joint-immobilizing braces are known to protect healthy and injured joints and to promote healing of certain injuries. Supports and braces are commonly used for injuries and other medical problems at the knee, thighs, elbow, waist, wrist and back. Common injuries that can be helped by a support include strained or torn ligaments, tendentious, arthritis, and pulled or strained muscles.

Plastic or "soft" supports are usually preferred over braces where the body part is generally healthy and the intent is to support it in order to prevent injury of a joint and surrounding tissue. Soft supports are also used to protect and promote the healing of injured members where there are no broken bones and the patient is mobile. A support may be worn, for example, before engaging in work or a sports activity that is expected to involve unusual stretching or load bearing. The elasticity of the support is important not only to provide supporting externally applied compression, but also to maintain the support in a selected position on the body. Ideally the support is constructed so that it flexes easily and interferes as little as possible with the normal range of motion of the body part. The elasticity of the support also accommodates changes in the size of the body part produced by physical exertion, changes in the condition of an injury (e.g., a reduction in swelling), or mere changes in the elevation of the body part, e.g., when an injured ankle is elevated.

The most common form of elastic support is a simple tubular sleeve of a stretch fabric such as the stretch nylon material used in ACE brand bandages and supports. Such a sleeve is pulled over and grips the body part to be protected as well as adjoining regions. When used on joints, the major problems are chafing and biting of the fabric during flexing, particularly at the interior of a joint such as the back of a knee or the "inside" of an elbow. Flexures of body parts and changes in body size can also result in a migration of the position of the support on the body.

Currently available supports do not provide the breathability necessary to prevent perspiration from forming where the support and skin are in contact and also have designs such that there is a seam located against the skin or behind the back of the knee that causes pinching or biting on the skin or behind the knee. In addition, current supports lack the sufficiency utilization around the patella and sufficient flexibility in attaching the support to the knee.

SUMMARY OF THE INVENTION

The present invention overcomes the problems identified in the background material by providing a laminated orthopedic support made from a unique blend of material that provides heat retention, compression with breathability, and quick wicking of perspiration away from the skin.

In particular, the present invention provides a laminated orthopedic brace made from a unique blend of material combining Airpreene™ material with Coolmax™ material as a liner. Airpreene™ material affords the properties of heat retention, compression and breathability, while Coolmax™ material wicks perspiration away from the skin and dries the area quickly. The combination of these materials provides compression and heat retention to the interior portion of the knee and comfort to the posterior aspect of the knee.

One embodiment of the present invention provides a laminated knee stabilizer having a pair of lateral seams reinforced with flexible metal stays on each side of the knee to avoid having to position a seam behind a knee. A pair of adjustable cinch straps are provided above and below the knee to add support and to enhance the overall function of the knee stabilizer. The knee stabilizer also has increased medial/lateral stability with the use of a polycentric hinges. The unique strapping system helps to maintain proper positioning and functioning of these hinges on the wearer. An alternative design for the knee stabilizer includes a polyaxial hinge in place of the metal stays, while both designs include a circular patella buttress that provides stabilization around the knee when properly mounted on the wearer.

Other embodiments of the present invention include an elbow brace with a moveable support, an ankle brace with multiple straps, a back brace and a wrist brace. Each of these supports and braces are made from this unique blend of material combining Airpreene™ material with Coolmax™ material as a liner. Airpreene™ material to provide the properties of heat retention, compression and breathability, with the Coolmax™ material wicking perspiration away from the skin to dry the area quickly. The combination of these materials in these products also provides the compression and heat retention needed to the interior portion of the body part without lost of comfort.

These and other aspects, features and advantages of the present invention will become apparent from the following detailed description taken in conjunction with the accompanying drawings.

DETAILED DESCRIPTION

Figure 1:
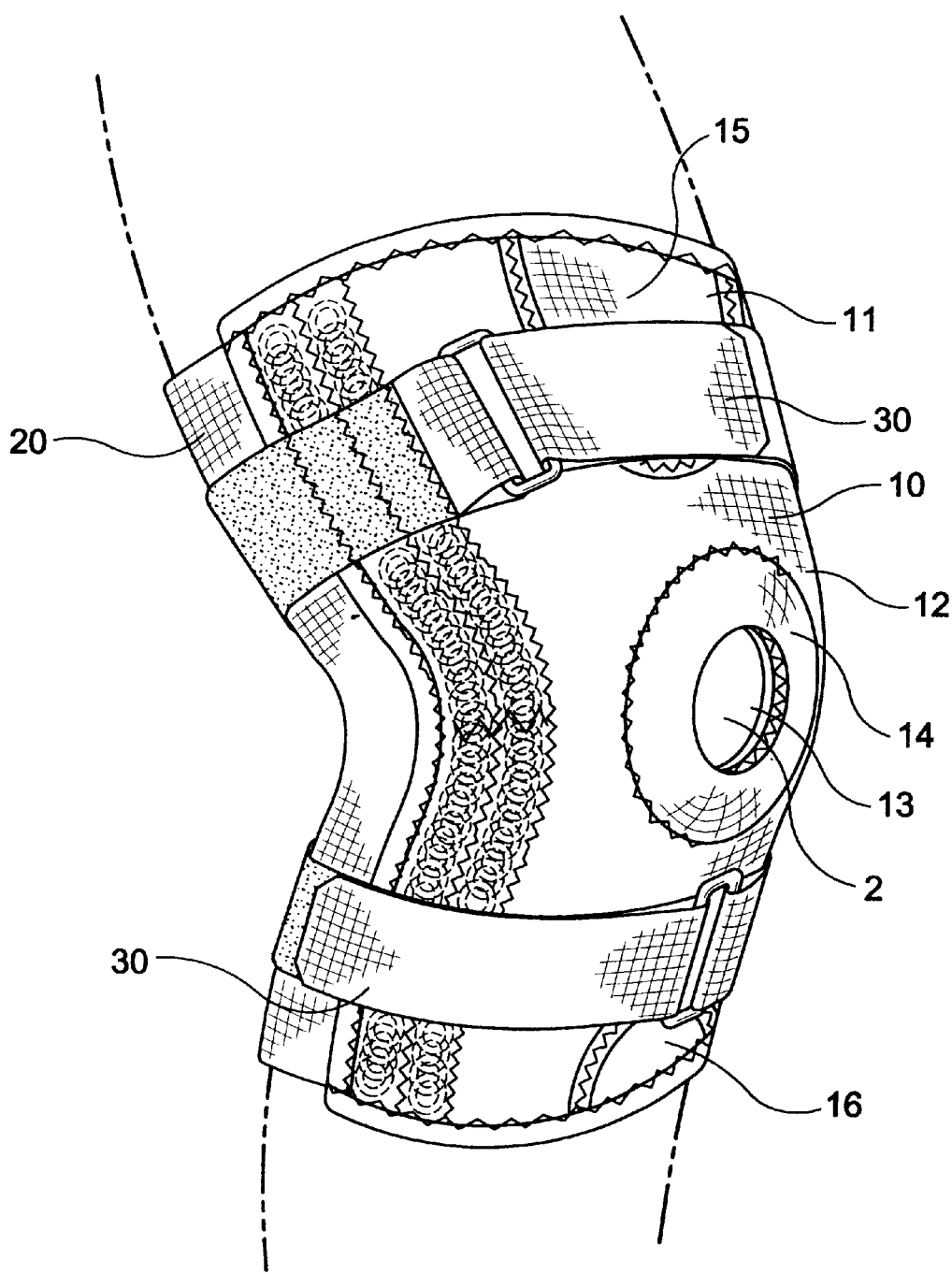
FIG. 1 is a perspective view of a knee stabilizer according to the present invention during use on a patient's knee.

FIG. 1 is a perspective view of a knee stabilizer 1 according to the present invention during use on a patient's knee 2.

Figure 3:
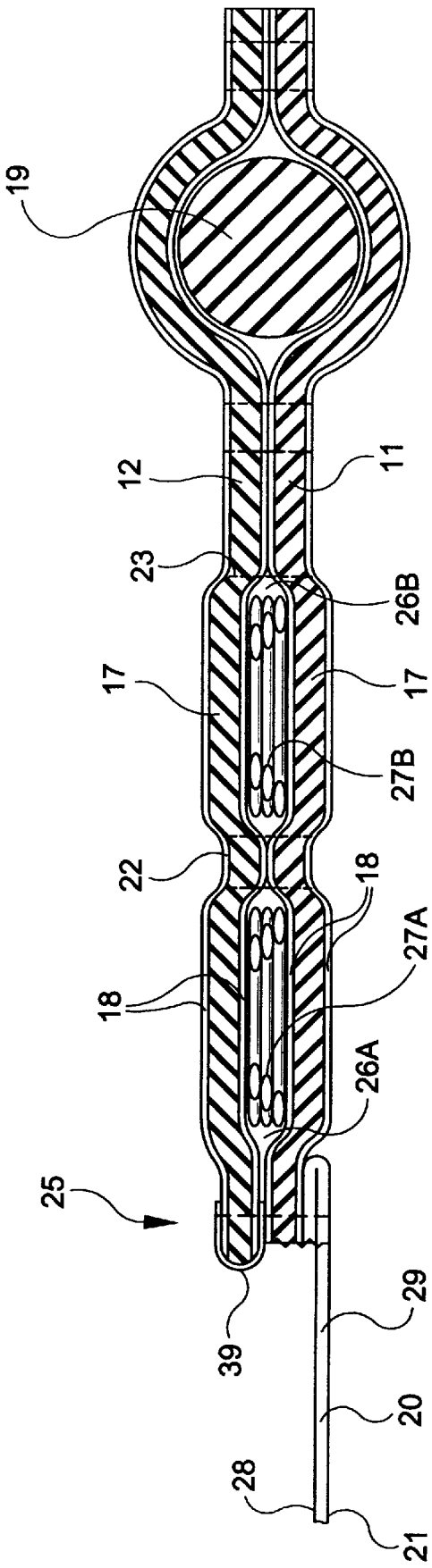
FIG. 3 is a cross-sectional view of a central portion of the knee stabilizer shown in FIG. 2.

As shown in FIG. 1 knee stabilizer 1 includes a front section 10 and a back panel 20. Front section 10 is a multi-layered material including an inner layer 11 and an outer layer 12. Both of these layers are preferably made of a material such as Airpreene™ material that is a flexible sheath of a closed-cell foam having a stretch fabric liner on both sides of a neoprene center. FIG. 3 more clearly shows a composition of inner layer 11 and outer layer 12. Both layers contain an inner material 17 consisting of a flexible sheath of a heat-retaining material such as a closed-cell foam such as neoprene having a plurality of holes therethrough and a pair of coextensive stretch fabric liners 18 on either side of inner layer 17 that is preferably made of a fabric such as stretch nylon or a polypropylene that wicks moisture (perspiration) and controls chaffing due to repeated relative movement of the liner with respective to the body part. As shown in FIG. 1 outer layer 12 includes an upper recess 15 and a lower recess 16 where there is only one layer of material, inner layer 11. Upper recess 15 and lower recess 16 provide improved adjustability by providing expansion and contraction at the upper and lower ends of knee stabilizer 1.

Front section 10 also includes an opening 13 surrounded by a circular patella buttress 14 to provide improved stabilization of knee stabilizer 1 on knee 2. As shown in FIG. 3, buttress 14 is formed by a foam ring 19 that is stitched between inner layer 11 and outer layer 12. Circular buttress 14 provides complete patella support for knee 2.

Figure 2:
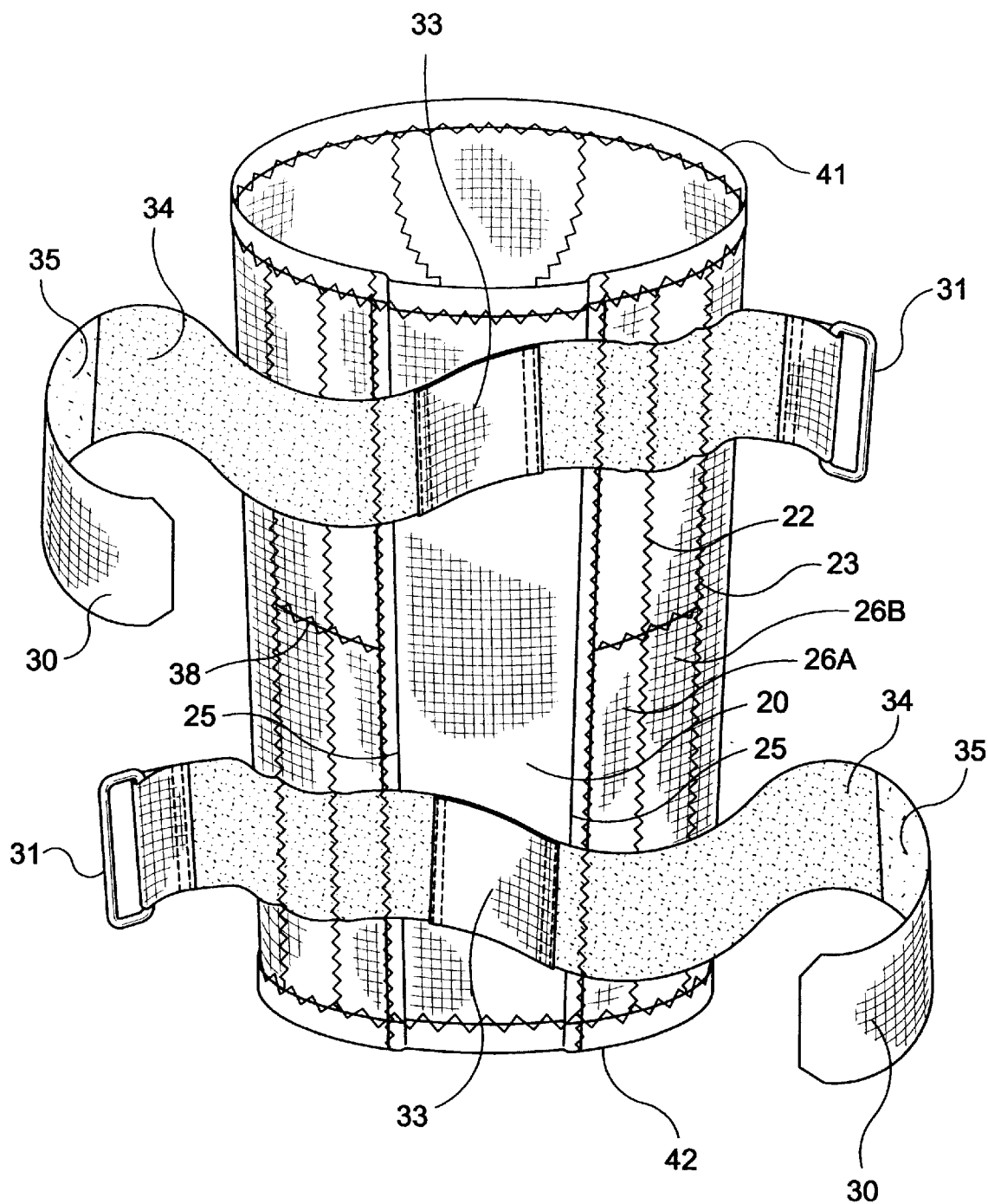
FIG. 2 is another perspective view of the knee stabilizer shown in FIG. 1, in an unlatched position with the patient's knee removed from the knee stabilizer.

As shown more clearly in FIG. 2, knee stabilizer 1 includes a back panel 20 that is attached to front section 10 at specially designed back seams 25. Back panel 20 is made of a unique blend of material that combines Airpreene™ material with Coolmax™ material as a liner. The Airpreene™ material, as described above, affords the property of heat retention, compression with breathability, while the Coolmax™ material laminated to the inside of knee stabilizer 1 wicks perspiration away from the skin behind knee 2 and dries the area quickly. As shown in FIG. 3, back panel 20 includes the center layer 29 formed from neoprene having holes therethrough, an outer layer 21 of stretch nylon or polypropylene, and an inner layer 28 formed from a specially designed Coolmax™ material.

Figure 4:
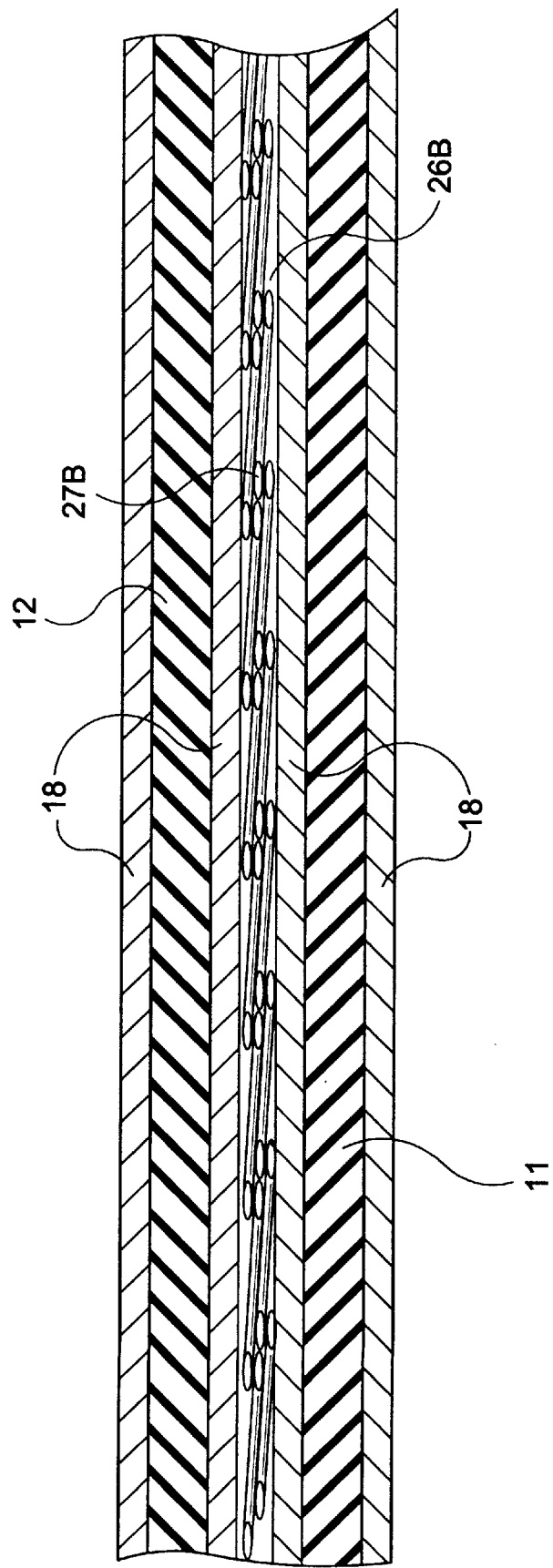
FIG. 4 is another cross-sectional view of the knee stabilizer shown in FIG. 2 along the seam.

Also is shown in FIGS. 3 and 4, a pair of pouches 26A and 26B are formed between inner layer 11 and outer layer 12 to receive specially designed compressed springs 27A and 27B that provide increased stability on each side of knee 2. Pouches 26A and 26B are formed between back seam 25 and center stitch 22 and between center stitch 22 and a front stitch 23 on both sides of back panel 20, where back panel 20 is attached to front section 10. As shown in FIG. 2, knee stabilizer also includes a pair of straps 30 with one located near upper end 41 of knee stabilizer 1 and the other attached at lower end 42 of knee stabilizer 1. Each of these straps 30 are specially designed to include a elastic section 33, a mesh section 34, and a hook section 35. Each strap 30 also includes a buckle 31 attached to one end of strap 30 to receive the other end of strap 30 after strap 30 is wrapped around the patient's leg. Hook material 35 is then overlaid onto mesh material 34 to provide a very flexible means of tightening strap 30 and securing it in position for use. Knee stabilizer 1 is used for chronic knee pain, arthritic knee changes, acute swelling; patella-femoral disorders; and the straps and stays help maintain its position on the knee.

Figure 5:
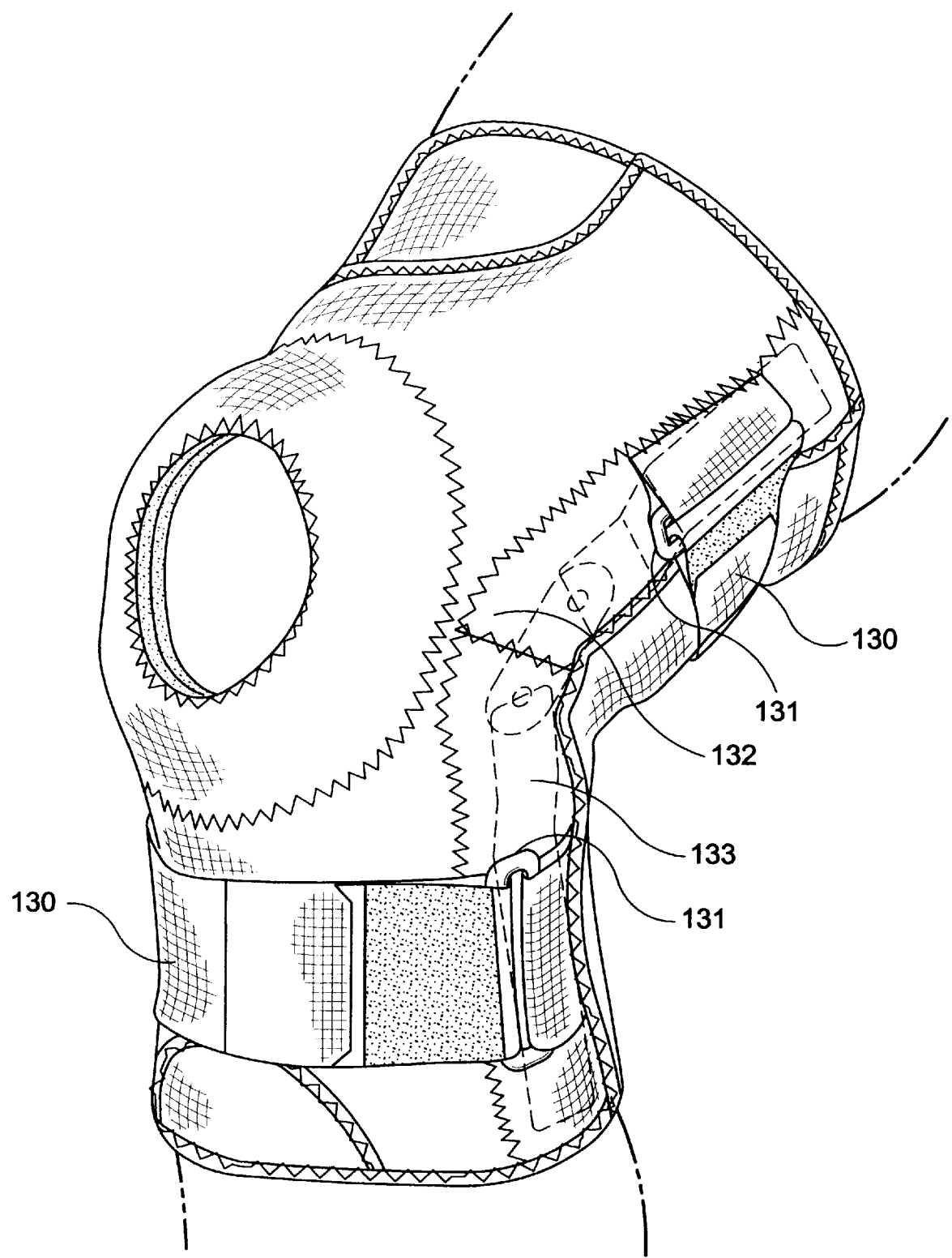
FIG. 5 is a perspective view of an alternative knee stabilizer according to the present invention during use on a patient's knee.

An alternative embodiment for the knee stabilizer, as shown in FIG. 5, includes a pair of removable straps 130 that are attached to a pair of buckles 131. Each end of each strap 130 is attached to a buckle 131 that is attached to and tightened to provide proper forces to the patient's leg. As shown in FIG. 5, this strap arrangement is used in knee stabilizer having a pair of polycentric hinges 133 each mounted in its own pouch 132 on either side of back panel 20 to provide the increased medial and lateral stability. In this embodiment the unique strapping system also helps to maintain proper positioning and functioning of these hinges when the knee stabilizer is in use by the patient. This device is usable for mild, acute or chronic sprain to medial/collateral and lateral/collateral ligaments of the knee. In this embodiment as in the earlier embodiment the Airpreene™ material affords the properties of heat retention, compression with breathability, and the Coolmax™ material wicks perspiration away from the skin and dries the area quickly.

Both of these knee stabilizers are stitched as shown in FIG. 3 to prevent any pinching or biting behind the back of the knee by eliminating seams in that location. To form the knee stabilizer, a zig-zag stitch 38 is used to greater a contour shape in inner layer 11 and outer layer 12, a zig-zag stitch is then sued to form the butress opening circle (cut out in the middle of each layer 11 and 12 and join these layers together, and then a merrow stitch is used to attach back panel 20 to inner layer 11, as shown in FIG. 3. Back panel 20 is then folded over and away from inner layer 11 and a edging 39 is wrapped around the edge of upper layer 12 and are both attached to the inner layer 11 and back panel 20 using a zig-zag stitch to form seam 25. Both of these seams 25 run laterally down each side of back panel 20 and, as shown in FIG. 3, provide a smooth surface on the inside of knee stabilizer 1 that will be in contact with the user's leg. In addition, the fabrication of this product results in the Coolmax material of the laminated fabric being in contact with the user's leg.

Figure 6:
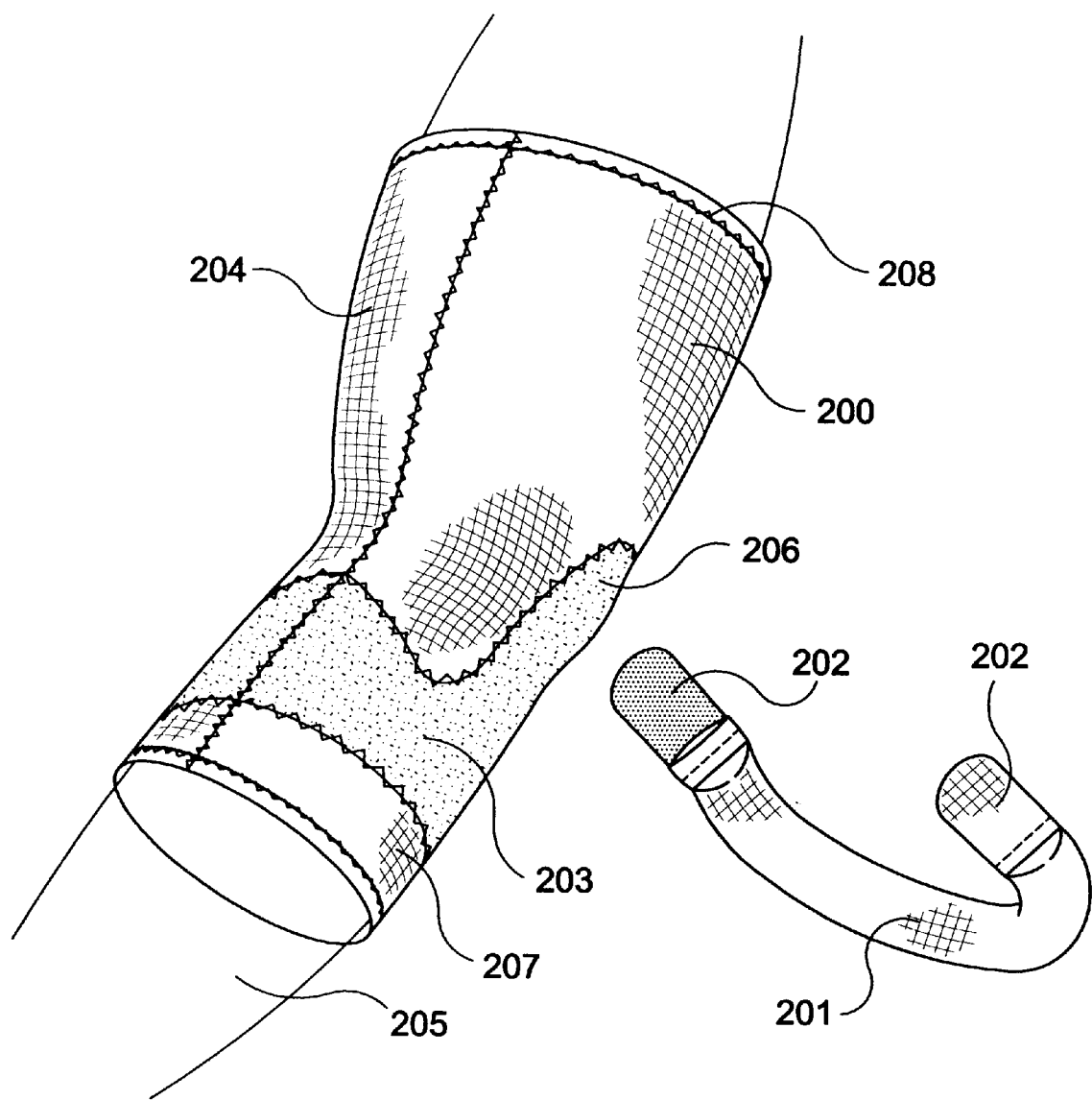
FIG. 6 is a perspective view of an elbow brace according to the present invention with its movable support removed during use on a patient's arm.
Figure 7:
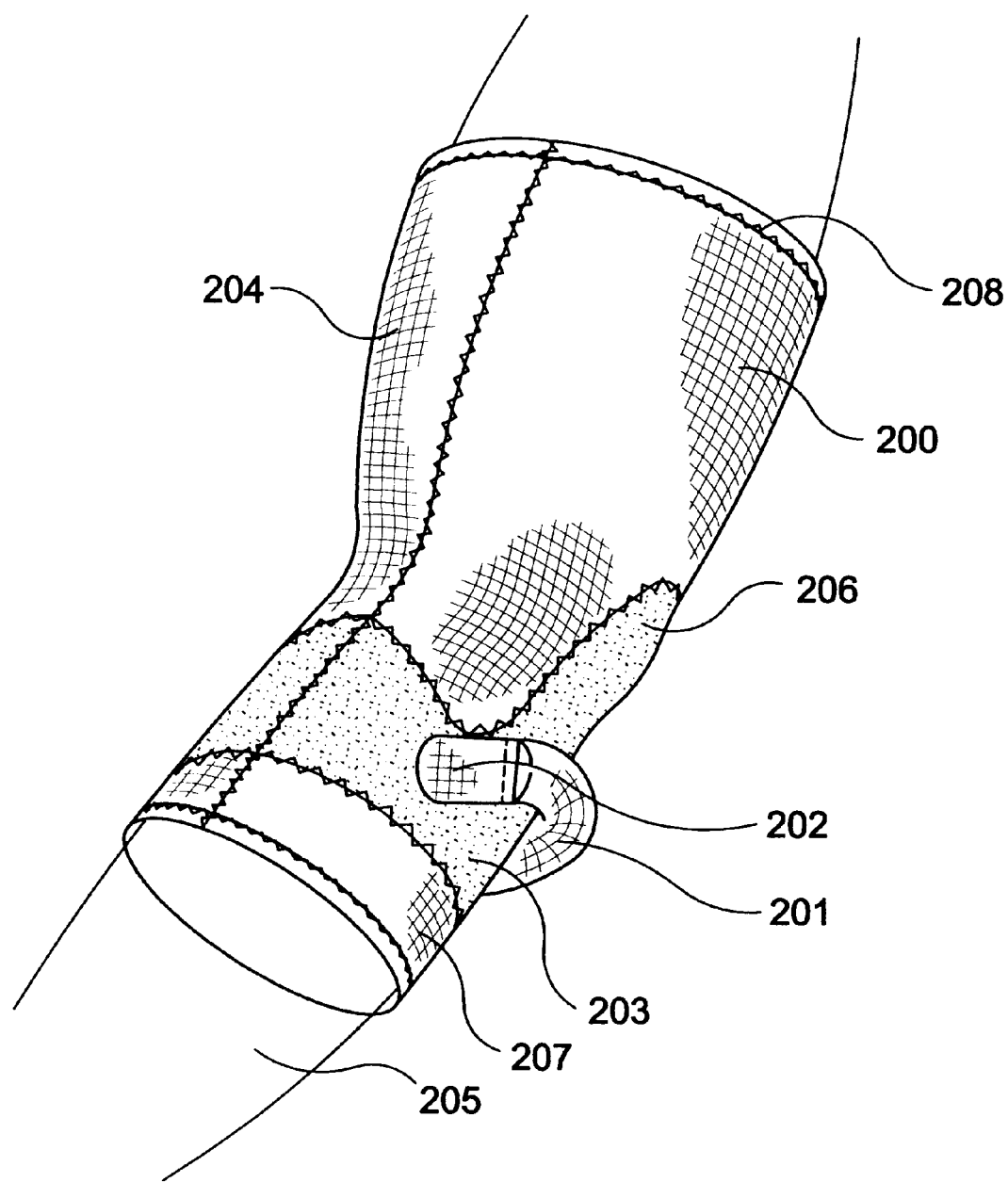
FIG. 7 is another perspective view of the elbow brace shown in FIG. 6, with its movable support attached during use on a patient's arm.

FIG. 6 is a perspective view of an elbow brace 200 according to the present invention with a movable support 201 removed during use on a patient's arm 205. As shown in FIG. 6, elbow brace 200 includes an upper section 204 and a lower section 207 with a special mesh section 203 therebetween encircling arm 205 and having an extension 206 extending up arm 205 adjacent the patient's elbow. FIG. 7 is another perspective view of elbow brace 200 shown in FIG. 6, with movable support 201 attached to mesh portion 203 during use on the patient's arm 205. Movable support 201 includes a pair of hook fasteners 202 at each end that are used to attach movable support 201 to the mesh portion of elbow brace 200. Moveable support 201 also provides individual tendentious relief and is formed by a foam cylinder 211 that is stitched between an outer layer of material 201.

Figure 8:
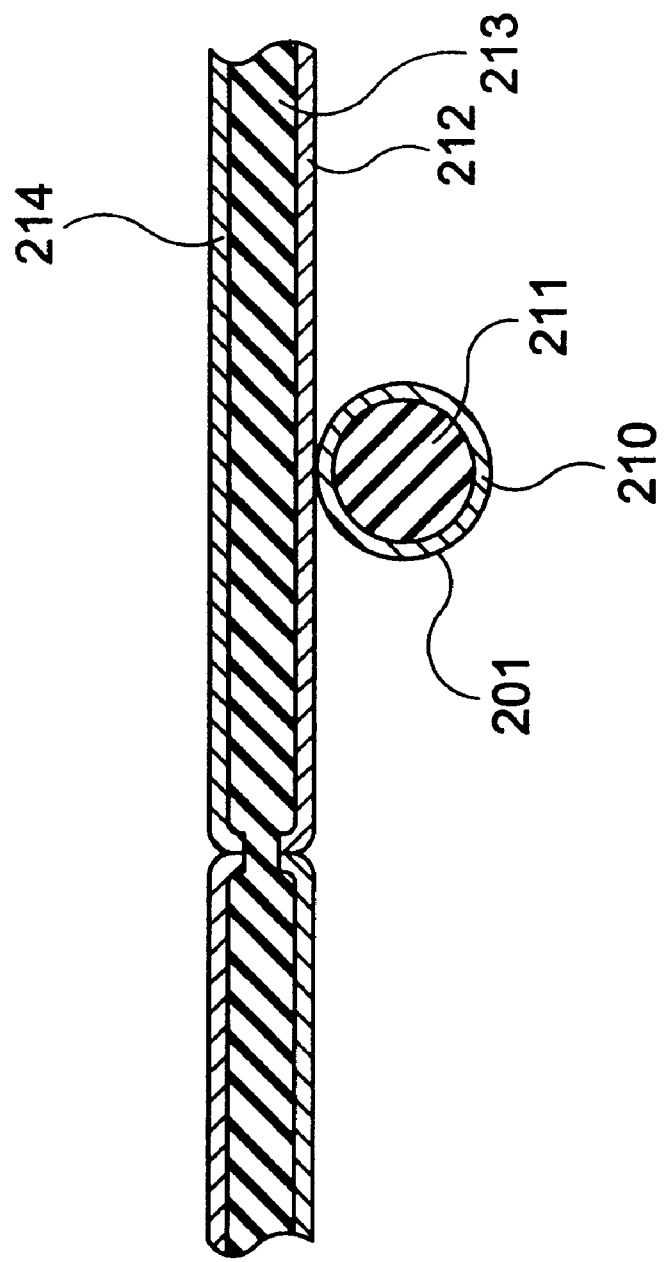
FIG. 8 is a cross-sectional view of a portion of the elbow brace and support shown in FIG. 7.

FIG. 8 is a cross-sectional view of a portion of elbow brace 200 and movable support 201 shown in FIG. 7. As shown in FIG. 8 elbow brace 200 incorporates the same unique material concept of the present invention which combines Airpreene™ material with Coolmax™ material as a liner. The Airpreene™ material 213 having a mesh material 212 laminated on one side and the Coolmax™ material 214 laminated to the other side provides the property of heat retention and compression with breathability, while the Coolmax™ material 214 inside elbow brace 200 whisks perspiration away from the skin in the vicinity of the patient's elbow and dries the area quickly. The present invention also minimizes bulk in the elbow crease when bending and movable support 201 provides a unique design that is fully adjustable to provide specific pressure where needed while preventing circulation from being cut off since it does not circumvent the forearm. In addition, an elliptical seam 208 near the top of elbow brace 200 provides optimal comfort during arm contraction. The exemplary elbow brace 200 shown here uses an Airpreene™ material that is 1.5 mm thick where it is laminated to the Coolmax™ material and a 3 mm thickness in the upper and lower sections 204 and 207, respectively.

Figure 9:
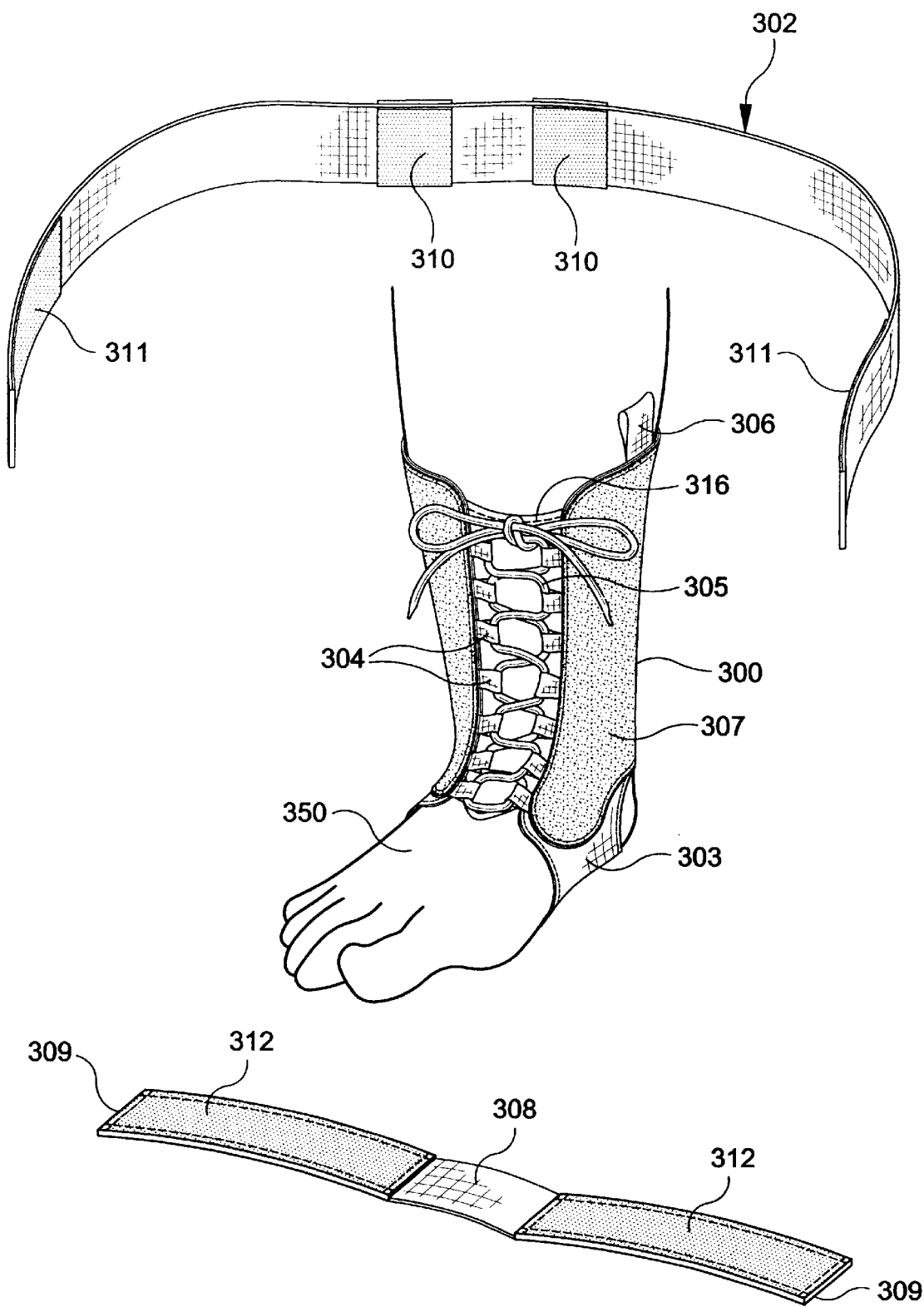
FIG. 9 is a perspective view of an ankle brace according to the present invention with multiple straps removed during use on a patient's foot.

FIG. 9 is a perspective view of an ankle brace 300 according to the present invention with multiple straps 301 and 302 removed during use on a patient's foot 350. As shown in FIG. 9, ankle brace 300 includes an outer mesh surface 307 that surrounds the patient's foot 350 having a stirrup 303 attached thereto and extending underneath the patient's foot 350. Ankle brace 300 also includes a plurality of eyelets 304 that are used to lace-up the front of ankle brace 300 using a lace 305. Lace 305 and eyelets 304 provide a quick and efficient means for attaching ankle brace 300 to a patient's foot 350 without causing any discomfort that would be associated with using metal eyelets. Ankle brace 300 has a streamlined design to fit into any shoe and also includes a Coolmax™ material 320 on its interior to whisk perspiration away from the patient's skin and dry the area quickly. Ankle brace 300 also incorporates the unique blend of material according to the present invention that combines an Airpreene™ material with the Coolmax™ material as the liner. Therefore, the Airpreene™ material affords the properties of heat retention and compression with breathability while the Coolmax™ material whisks perspiration away from the patient's skin.

As shown in FIG. 9, ankle brace 300 totally surrounds the patient's ankle and includes a solid panel 316 behind eyelets 304 to prevent irritation to the patient's leg and also provide the whisking of perspiration away from the patient's skin. Eyelets 304 are made of nylon. Ankle brace 300 also includes a pair of pull tabs 306 that aid the patient in pulling ankle brace 300 onto foot 350 as you would a sock or boot. After ankle brace 300 has been pulled onto foot 350 the patient uses lace 305 to firmly attach ankle brace 300 thereto.

Figure 10:
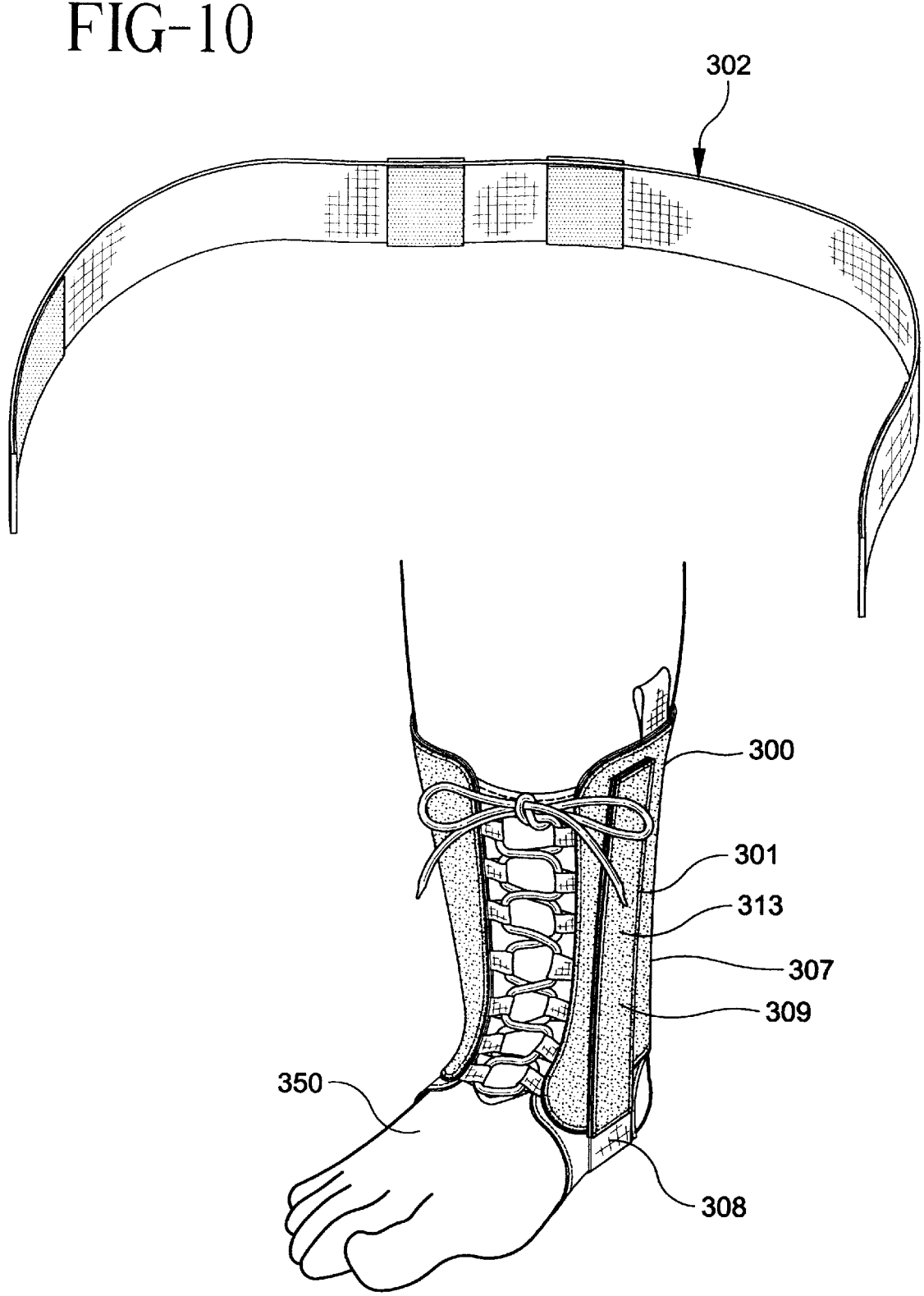
FIG. 10 is another perspective view of the ankle brace shown in FIG. 9, showing the lower strap attached to the ankle brace during use on a patient's foot.
Figure 11:
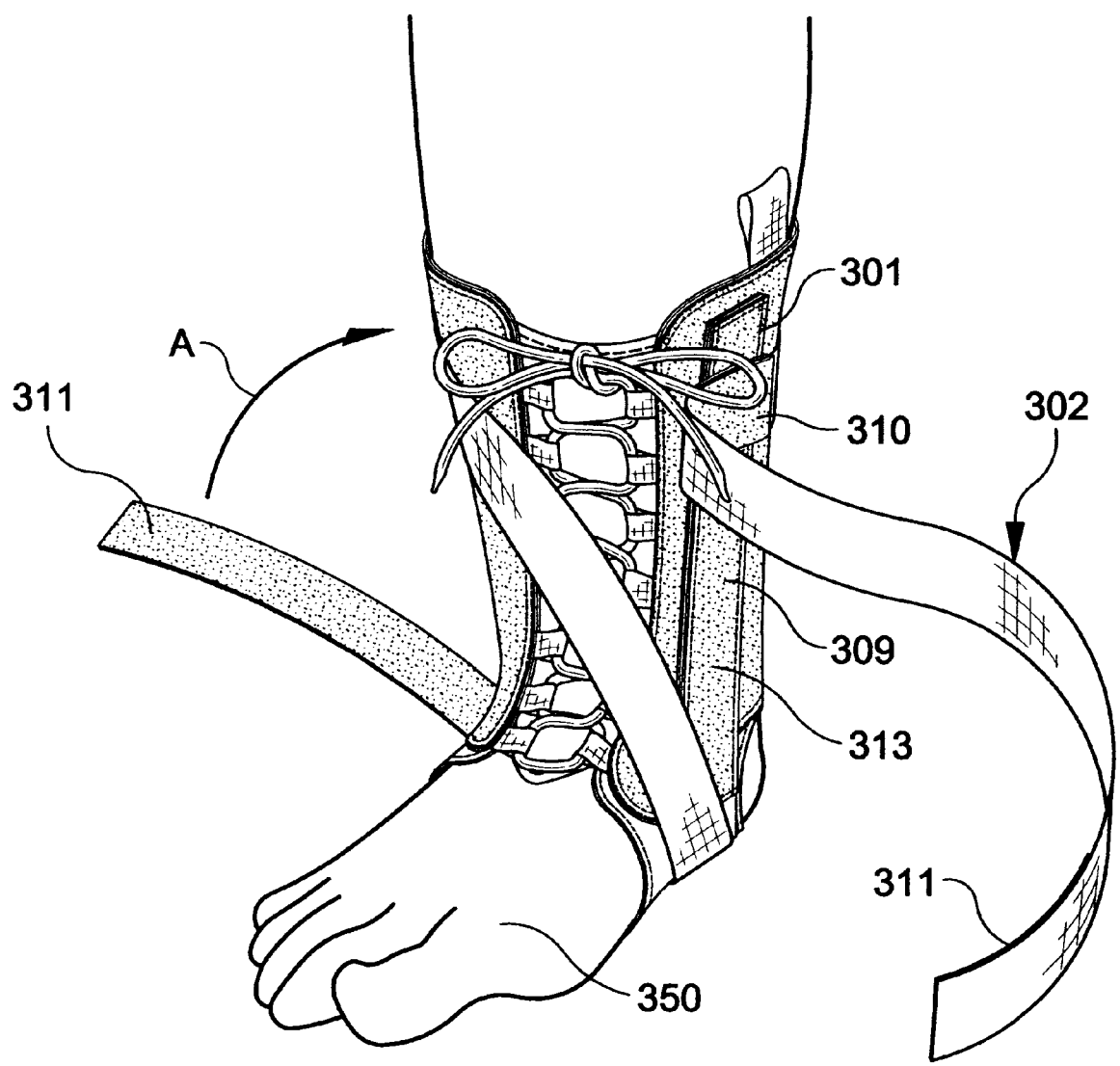
FIG. 11 is another perspective view of the ankle brace shown in FIGS. 9 and 10, showing the upper strap in the process of being attached thereto during use on a patient's foot.
Figure 12:
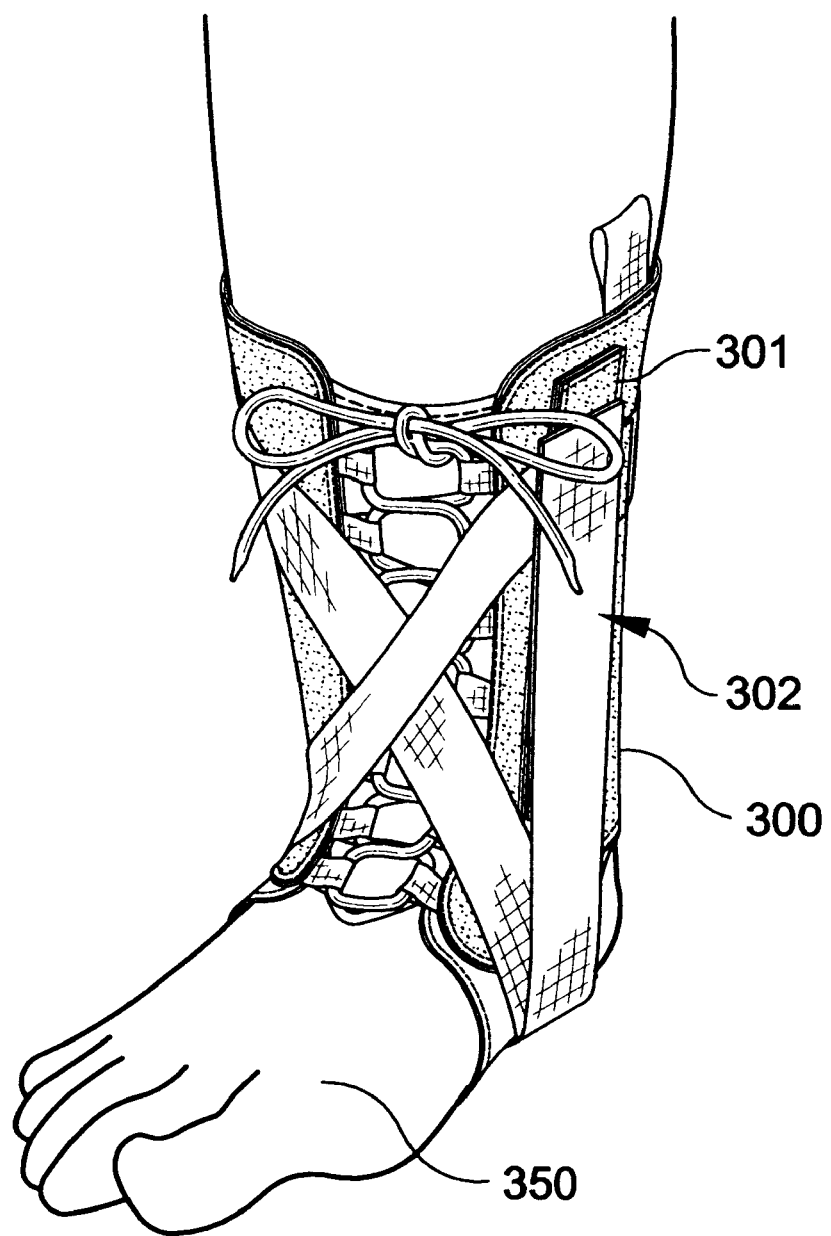
FIG. 12 is another perspective view of the ankle brace shown in FIGS. 9, 10 and 11, showing the upper strap full attached to the ankle brace during use on a patient's foot.

As shown in FIG. 9, a pair of straps 301 and 302 are provided to simulate professional ankle taping and to control rear foot and fore foot stability. Strap 301 includes a stirrup 308 that goes under foot 350 and a pair of extensions 309 each having a hook material 312 on one side and a mesh material 313 on the other. As shown in FIG. 10, strap 301 is attached to foot 350 by interaction between hook material 312 on each extension 309 mating with mesh material 307 on the sides of ankle brace 300. Then, strap 302 having a pair of hook material patches 310 and hook material extensions 311 is wrapped around the back of ankle brace 300 such that hook material patches 310 attach to mesh material 313 on strap 301 and then strap 302 is wrapped over the top of foot 350, under foot 350 such that the hook material on extension 311 can be attached to the mesh material 313 on strap 301 located on the side of ankle brace 300. The wrapping operation is clearly shown in FIG. 11 and indicated by arrow A and the final configuration is shown in FIG. 12.

Figure 13:
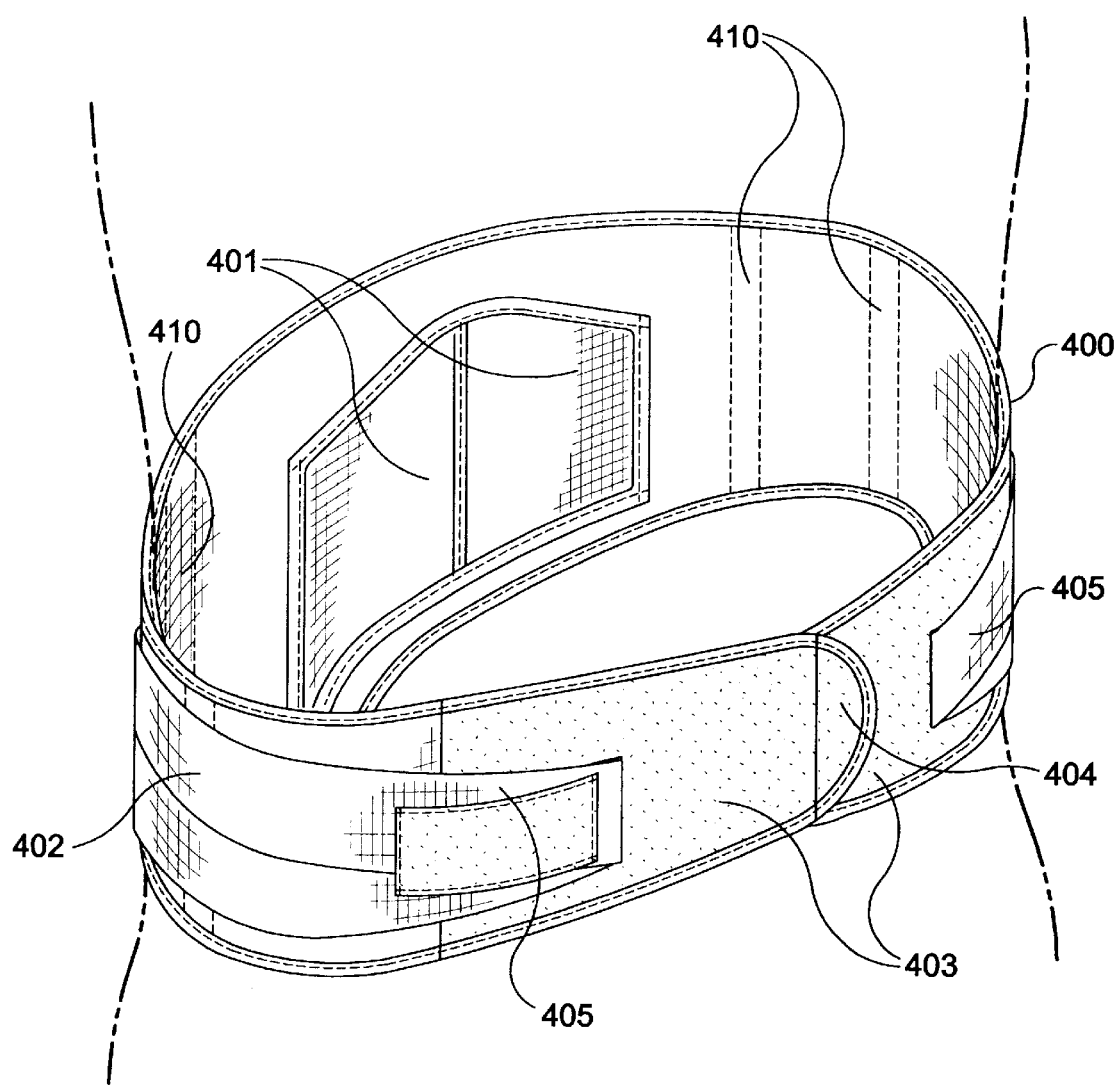
FIG. 13 is a perspective view of a fully assembled back support according to the present invention during use on a patient.

FIG. 13 is a perspective view of a fully assembled back support 400 according to the present invention during use on a patient. Back support 400 also incorporates the unique material concept of the present invention by combining Airpreene™ material 407 with Coolmax™ material 409 as a liner. As shown in FIG. 13, back support 400 includes a pair of lumbar pads 401 that provide maximum support to a patient's back, a dual strap system having an outer strap 402 that is attached at hook tabs 405 to a mesh area 403 at the front of back support 400. In addition, the front of back support 400 includes a connector 404 having a hook fastener thereon that attaches to mesh area 403 to provide a fully adjustable back support 400 while firmly holding back support 400 on the patient. In addition, back support 400 includes a slim line contour design with lumbar pads 400 positioned for lumbo-sacral support while still providing a back support that is thin enough to wear under clothing. Abdominal control is provided with overlapping outer strap 402, which is also non skid to limit migration on back support 400. Back support 400 therefore effectively helps the patient to maintain proper biomechanical positioning of the lower back during activity or while sitting or standing.

Figure 14:
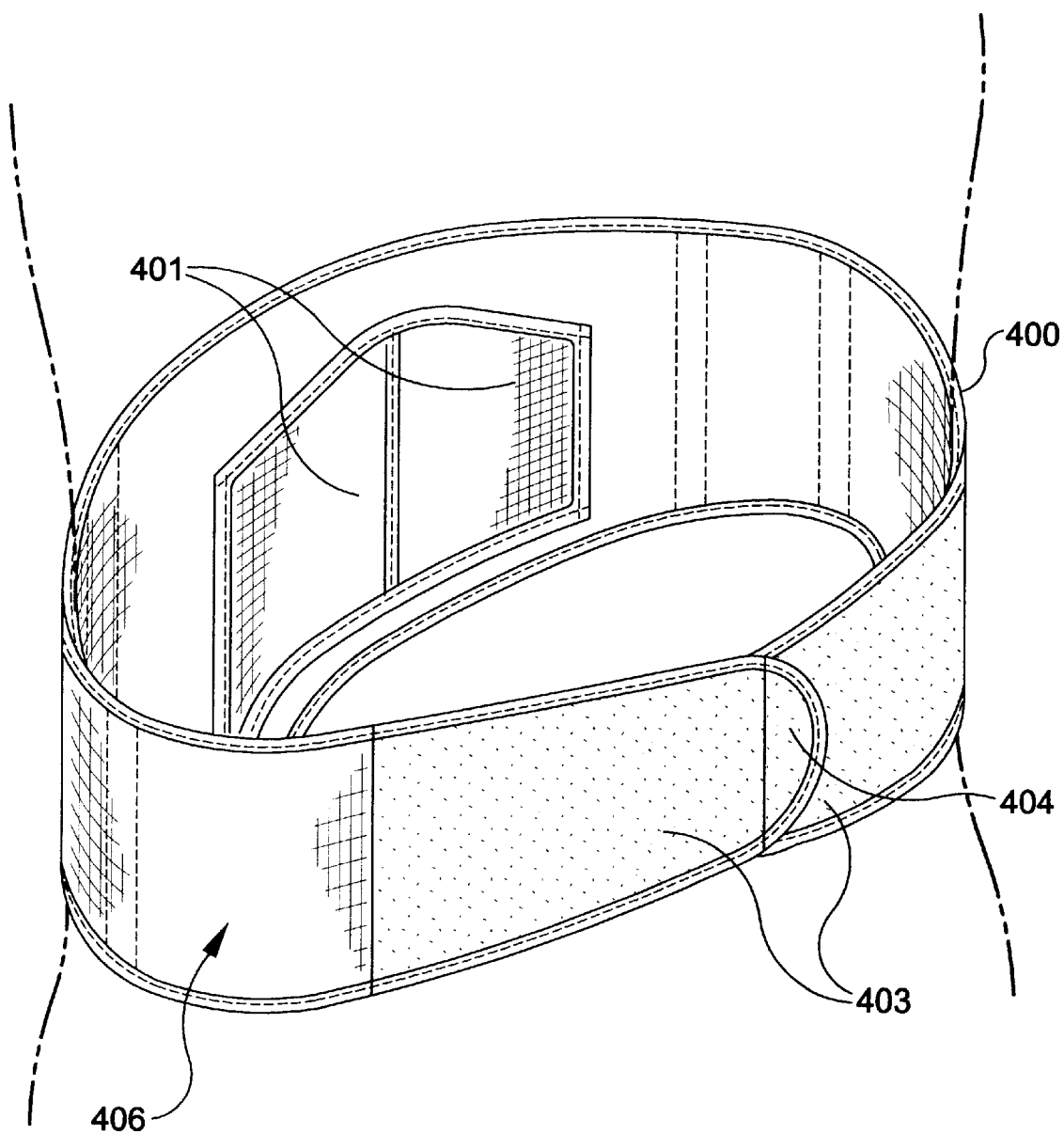
FIG. 14 is another perspective view of the inner shell of the back support shown in FIG. 13 during use on a patient.
Figure 15:
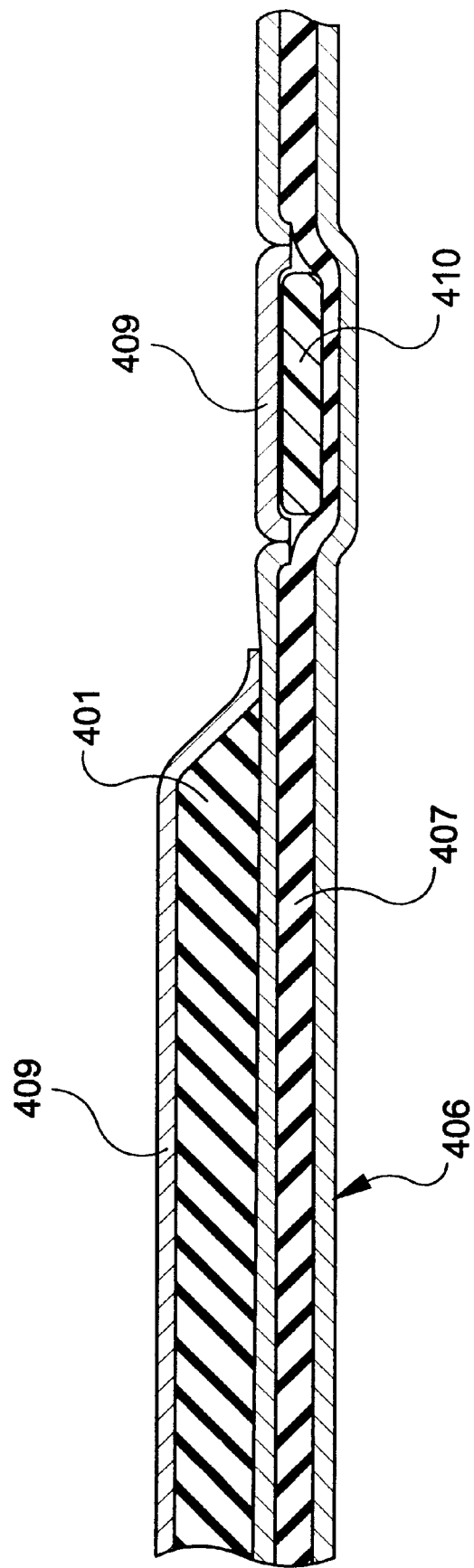
FIG. 15 is a cross-sectional view of a portion of the back support shown in FIG. 14.

FIG. 14 more clearly shows inner shell 406 of back support 400 during use on a patient with outer strap 402 removed. FIG. 15 is a cross-sectional view of a portion of back support 400, shown in FIG. 14, that more clearly shows Airpreene™ material 407, lumbar pad 401 and Coolmax™ material 409 laminated to one side of inner shell 406 such that the Coolmax™ material 409 whisks perspiration away the skin adjacent to inner shell 406 to dry the area quickly. FIG. 15 also shows one of a plurality of stays 410 laterally located around the circumference of inner shell 406 to ensure correct posture and abdominal support for the patient while wearing back support 400.

Figure 16:
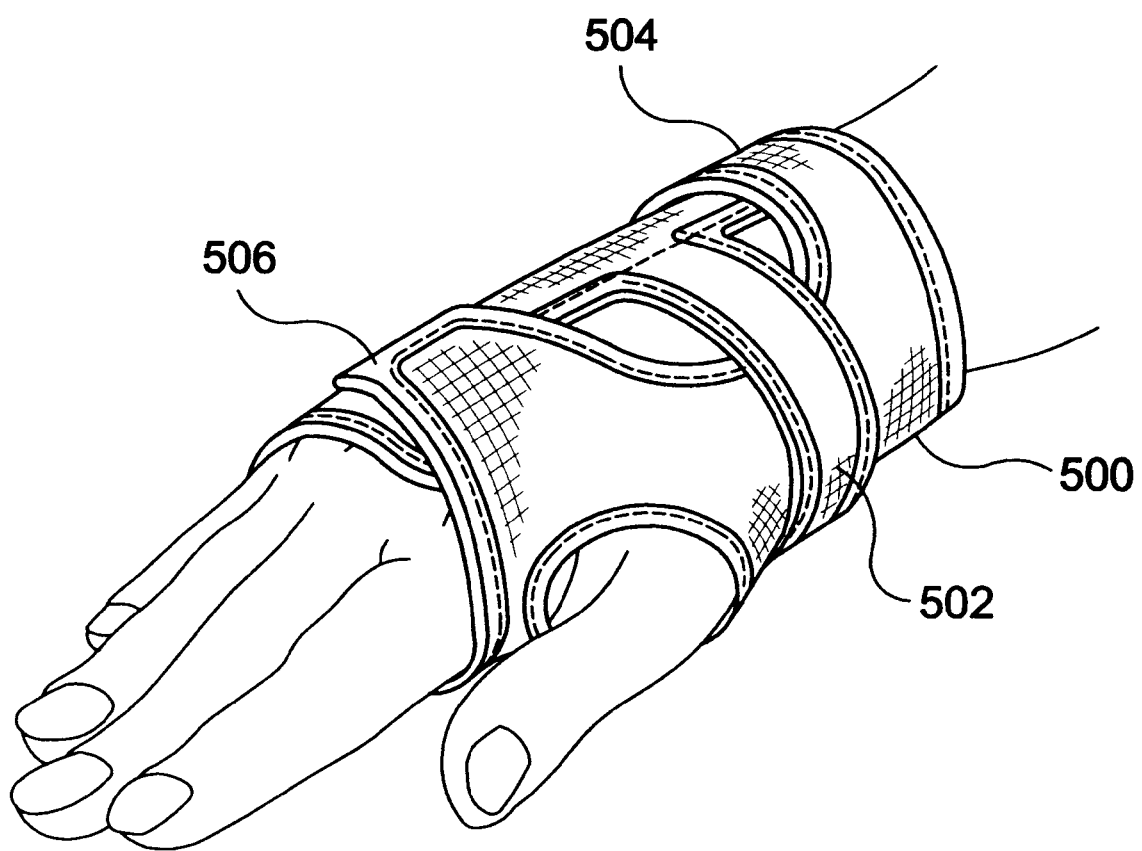
FIG. 16 is a perspective view of a wrist brace according to the present invention with during use on a patient's hand.
Figure 17:
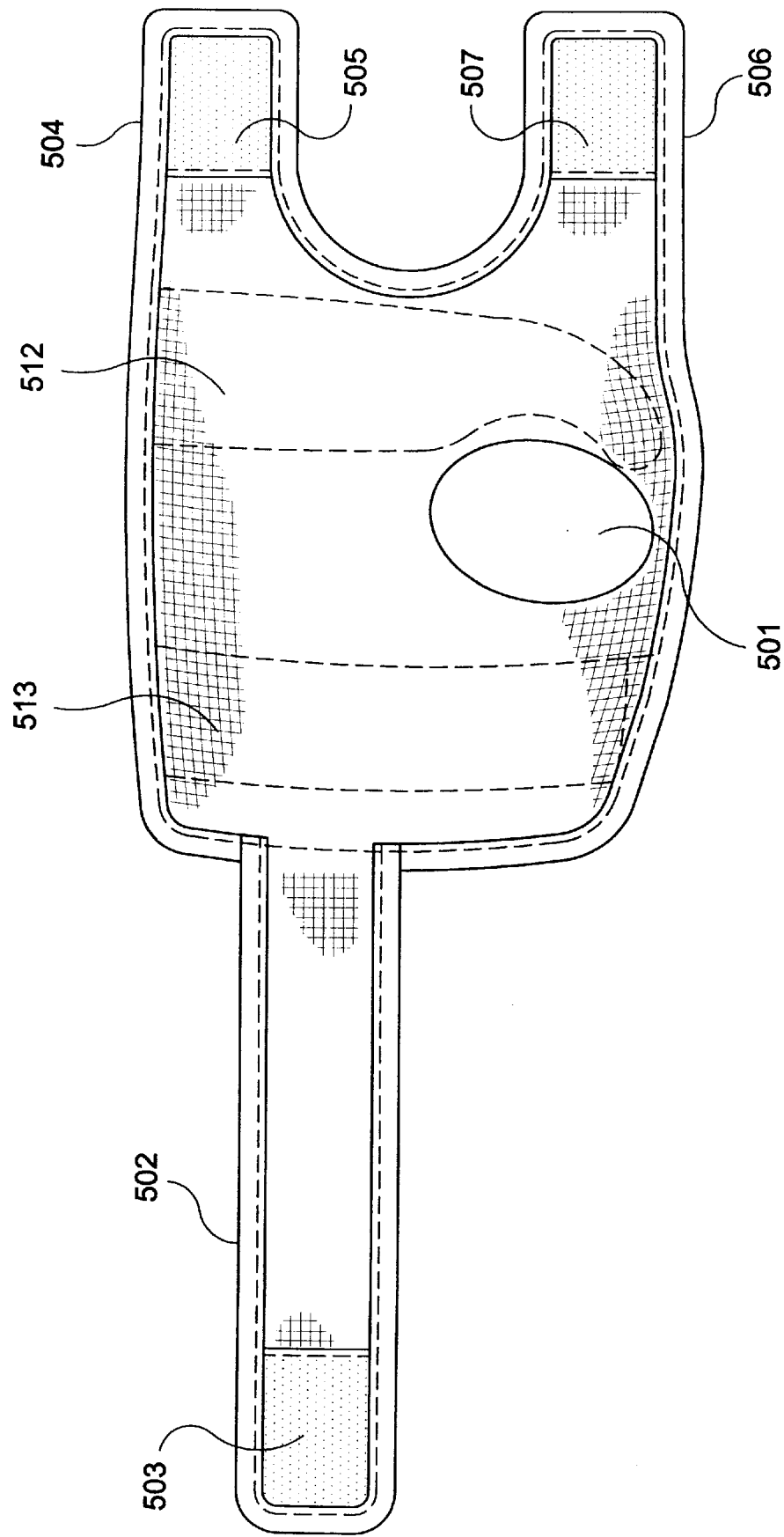
FIG. 17 is a plan view of the inside of the wrist brace shown in FIG. 16.
Figure 18:
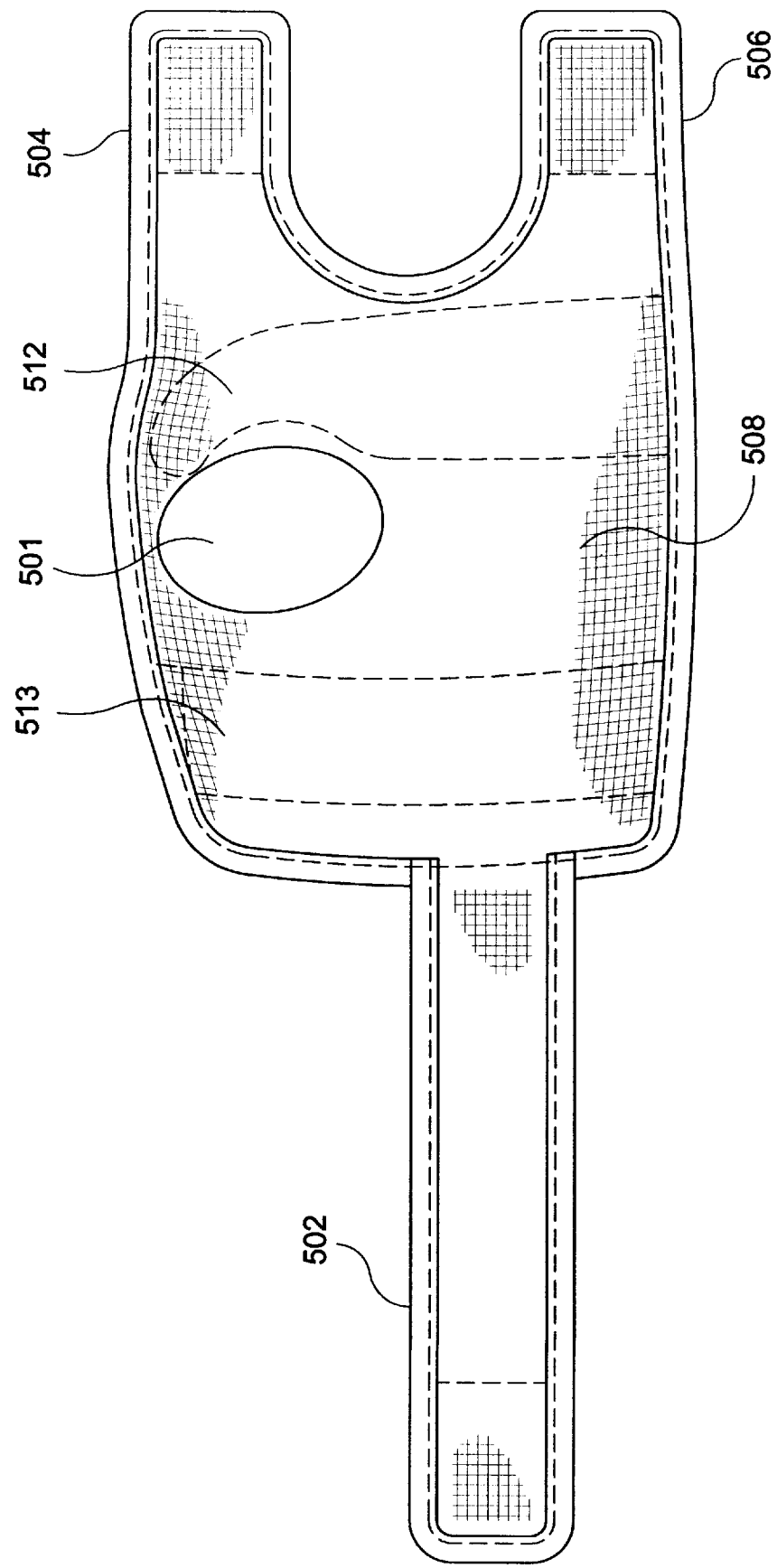
FIG. 18 is a plan view of the outside of the wrist brace shown in FIG. 16.

FIG. 16 is a perspective view of a wrist brace 500 according to the present invention during use on a patient's hand. As shown in FIGS. 17 and 18 wrist brace 500 includes a hole 501 for receiving the patient's thumb, a pair of outer straps 504 and 506 and a central strap 502. Strap 506 wraps around the patient's hand between the patient's thumb and index finger and includes a hook material 507 that attaches to a mesh material 508 on the exterior of wrist brace 500. Strap 504 extends around the other end of the patient's wrist and likewise is attached using a hook material 505 and mesh material 508. Central strap 502 wraps around the patient's wrist in the opposite direction and also attaches using a hook material 503 and mesh material 508.

Figure 19:
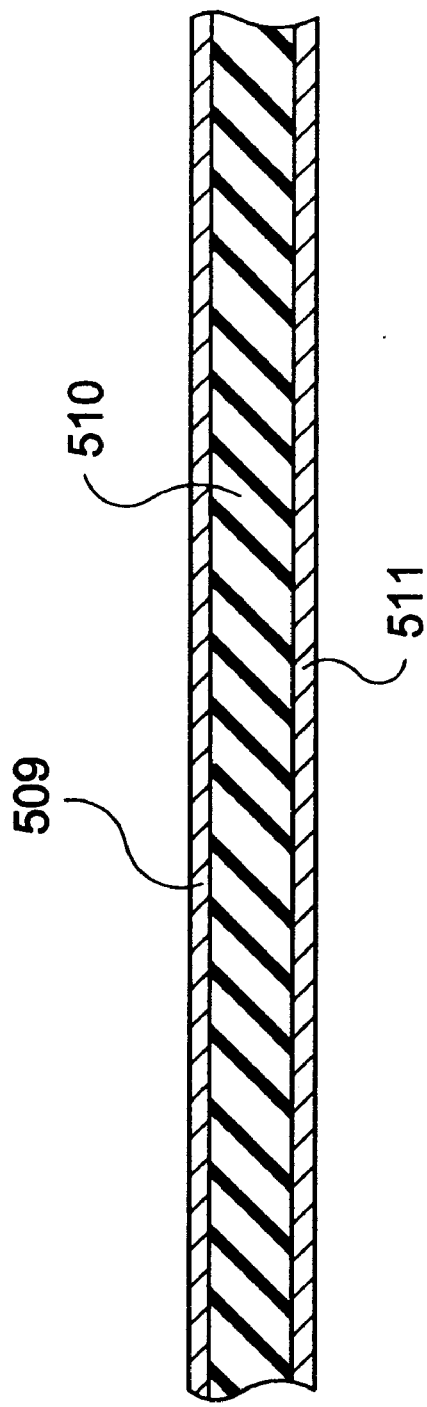
FIG. 19 is a partial cross-sectional view of the wrist brace shown in FIG. 17.

By providing a wrist brace wherein its outer surface is substantially all mesh material 508 attachment of straps 502, 504 and 506 are made easier and more flexible for the patient. Wrist brace 500 also includes the unique material concept of the present invention that combines an Airpreene™ material 510 with a Coolmax™ material 511 as a liner adjacent to the patient's skin to whisk perspiration away from the patient's skin and dry the area quickly. The Airpreene™ material 510 affords the properties of heat retention, compression with breathability. FIG. 19 more clearly shows the Coolmax™ material 511 laminated onto the Airpreene™ material 510 together with the lamination of mesh material 508 on the other side of the Airpreene™ material 510 or the outer surface of wrist brace 500. Wrist brace 500 provides sufficient support to fill all needs of the patient such as stability without sacrificing mobility for function, can incorporate a removable splint in a pocket 513, the universal adjustable strapping system, described above, and a low profile interior spoon (not shown) in the patient's palm located in a pocket 512 to allow the patient to participate in activity while still affording stability.

In the foregoing discussion, it is to be understood that the above-described embodiments of the present invention is simply illustrative of various features that can be used in a variety of orthopedic braces. Other suitable variations, modifications, applications, and combinations of these features could be made to or used in this embodiment and still remain within the scope of the present invention.

What is claimed is:

1. An orthopedic brace made from a unique lamination of material that provides heat retention and compression with breathability while also providing whisking of perspiration away from the patient's skin to dry the patient's skin area quickly while wearing said orthopedic brace, said orthopedic brace comprising:

an inner shell made from said unique lamination of material; and a pair of lumbar pads in said inner shell to provide additional abdominal support for the patient while wearing said orthopedic brace.

2. The orthopedic brace according to claim 1, wherein an inner layer of said inner shell is in contact with the patient's skin and is made of a material that whisks perspiration away from the skin to dry the skin quickly.

3. The orthopedic brace according to claim 1, further comprising a plurality of stays laterally located around the circumference of said inner shell to ensure correct posture and abdominal support for the patient while wearing said orthopedic brace.

\* \* \* \* \*